(12) United States Patent
Rouchon

(10) Patent No.: US 9,851,335 B2
(45) Date of Patent: Dec. 26, 2017

(54) METHOD AND SYSTEM FOR ANALYZING A GASEOUS FLUID COMPRISING AT LEAST ONE RARE GAS BY MEANS OF A GETTERIZING SUBSTRATE

(71) Applicant: IFP Energies nouvelles, Rueil-Malmaison (FR)

(72) Inventor: Virgile Rouchon, Saint-Cloud (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 435 days.

(21) Appl. No.: 14/220,644

(22) Filed: Mar. 20, 2014

(65) Prior Publication Data

US 2014/0283580 A1  Sep. 25, 2014

(30) Foreign Application Priority Data

Mar. 25, 2013 (FR) ...................... 13 52656

(51) Int. Cl.
  *C01B 23/00* (2006.01)
  *G01N 33/00* (2006.01)
  *G01N 1/22* (2006.01)
  *G01N 30/72* (2006.01)

(52) U.S. Cl.
  CPC ..... *G01N 33/0016* (2013.01); *C01B 23/0084* (2013.01); *G01N 1/2202* (2013.01); *G01N 1/2214* (2013.01); *G01N 33/0014* (2013.01); *C01B 2210/004* (2013.01); *G01N 30/7206* (2013.01); *G01N 33/0036* (2013.01)

(58) Field of Classification Search
  CPC .................................................. C01B 23/0084
  USPC ........................................................ 73/23.2
  See application file for complete search history.

(56) References Cited

U.S. PATENT DOCUMENTS

| | | | | |
|---|---|---|---|---|
| 6,422,824 B1* | 7/2002 | Lee | ......................... | F04B 37/02 313/553 |
| 2002/0035921 A1* | 3/2002 | Ishihara | ................. | B01D 53/22 95/45 |
| 2002/0093003 A1* | 7/2002 | Conte | ................... | B22F 3/1146 252/181.1 |
| 2007/0199824 A1* | 8/2007 | Hoerr | ..................... | B05B 5/025 205/80 |
| 2009/0118498 A1* | 5/2009 | Subramaniam | .... | B01D 53/1493 544/47 |

\* cited by examiner

*Primary Examiner* — Laura Martin
*Assistant Examiner* — Alex Devito
(74) *Attorney, Agent, or Firm* — Fitch, Even, Tabin & Flannery, LLP

(57) ABSTRACT

The invention relates to a method and a system for analyzing rare gases present in a gaseous fluid (1). According to the invention, initially, the rare gases are extracted from the gaseous fluid by trapping by means of a getterizing substrate (5), then superconcentration of the rare gases is produced before injection (8) into the measuring instruments (9). By virtue of the invention, it is possible to increase the partial pressure of the rare gases in the gases to be analyzed before their injection into the analysis instruments.

24 Claims, 1 Drawing Sheet

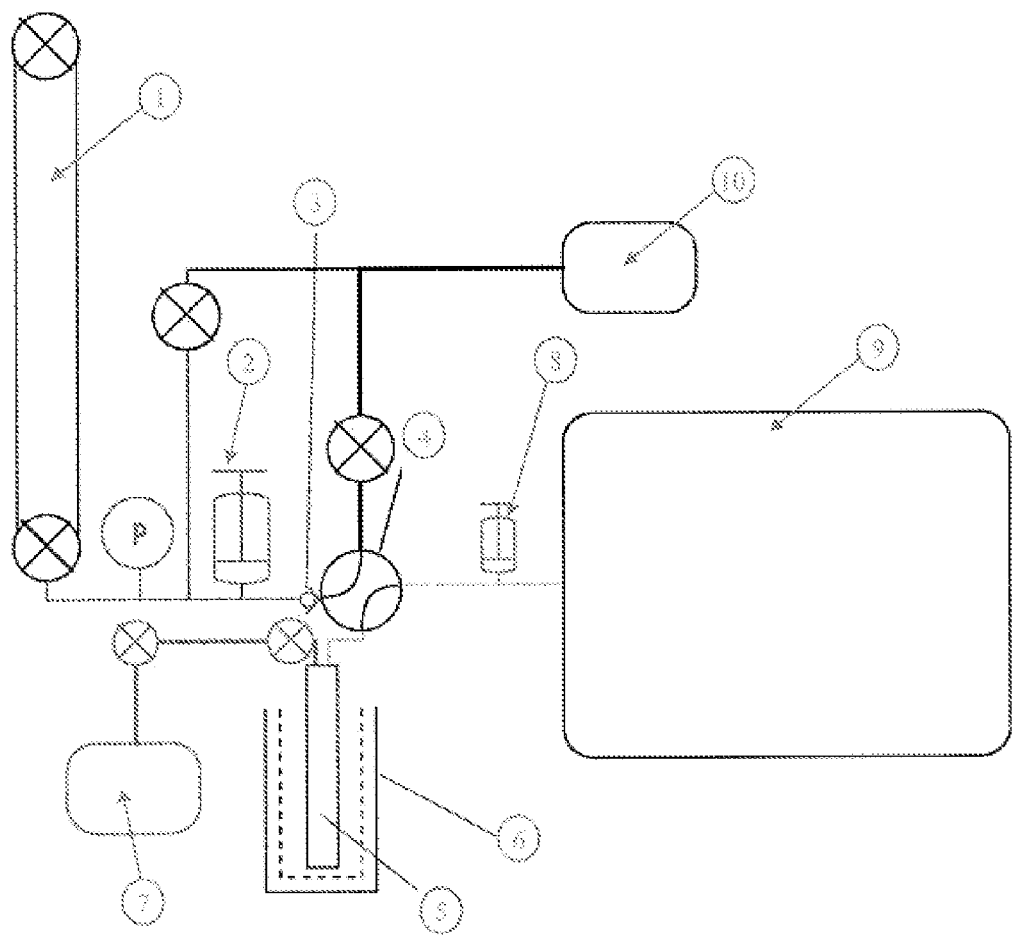

METHOD AND SYSTEM FOR ANALYZING A GASEOUS FLUID COMPRISING AT LEAST ONE RARE GAS BY MEANS OF A GETTERIZING SUBSTRATE

The present invention relates to the field of the analysis of gases, notably gases taken from geological reservoirs.

In order to obtain the best knowledge of the geological reservoirs, it is advantageous to determine the composition of the gases which are contained therein. These gases notably comprise non-radioactive rare gases (also called noble gases or inert gases): helium He, neon Ne, argon Ar, krypton Kr, xenon Xe. These are almost non-reactive chemical elements, belonging to Group 18 of the periodic table of elements, in the form of gases in normal temperature and pressure conditions. They are monoatomic, colorless and odorless. These gases are called inert because they exhibit almost no chemical reactivity.

The study of rare gases in the field of natural gases makes it possible to contribute to the understanding of the origin of the natural gas, and of the natural processes that have led to its evolution within the geological reservoirs. This evolution is generally characterized by the superposition of different chemical, biological and physical processes, which engender modifications of the elementary and isotopic composition of the gas, including notably that of the rare gases. The very great interest in the isotopy of He for tracing the origin of $CO_2$ in sedimentary, crustal or mantel basins can be cited in particular, as well as the interest in the elemental fractionations of certain isotopes of Ne, of Ar and of Kr for identifying the different phase balances (water, oil, gas) that have marked the history of a fluid (for example: U.S. Pat. No. 4,833,915). In the context of gas storage, the rare gases are effective leak tracers and can form the basis of computations of mass balances of the chemical state of the stored gas (example: patents WO2010-049608; FR 2 938 068).

With a view to the industrial application of the analysis of rare gases in the oil and gas field, there is a necessary need to develop an analysis system that is compact, robust and rapid. Knowing the analytical constraints on rare gases (abundancy, isotopy, sample volumes, necessary analytical accuracy), developments have focused on an analysis by gaseous phase chromatography coupled with mass spectrometry. These instruments are widely available in the market and their reliability is now proven. On the other hand, the low abundance of rare gases in nature, specifically in the field of hydrocarbons, demands a preprocessing of the gases to prepare the rare gases for the analysis conditions (volume, pressure, etc.), which entails a rig that is bulky and often tailor-made by competent laboratories. These days, these systems are ultravacuum preparation lines, coupled to mass spectrometers with magnetic or quadrapolar segments.

The invention relates to a method and a system for analyzing rare gases present in a gaseous fluid. According to the invention, initially, the rare gases are extracted from the gaseous fluid by trapping by means of a getterizing substrate, then a superconcentration of the rare gases is produced before injection into the measuring instruments. By virtue of the invention, it is possible to increase the partial pressure of the rare gases in the gases to be analyzed before their injection into the analysis instruments. Thus, the advantages lie mainly in the fact that the invention provides the possibility of using analysis instruments that are more commonplace than those used these days for the analysis of rare gases, and therefore a reduction of maintenance costs, the simplicity of the method and of the system.

The Method and System According to the Invention

The invention relates to a method for analyzing a gaseous fluid comprising at least one rare gas. For this method, the following steps are carried out:

a) the vacuum is created in an accumulation chamber comprising a getterizing substrate, said getterizing substrate being suitable for trapping the components of said gaseous fluid except for said rare gas;

b) the flow rate of said fluid entering into said accumulation chamber is controlled by means of a flow rate restrictor;

c) said rare gas is extracted and accumulated from said gaseous fluid by the passage of said gaseous fluid into said getterizing substrate of said accumulation chamber;

d) said extracted rare gas is compressed so that the pressure and the volume of said compressed rare gas are adapted to the pressure and the volume of said analysis; and e) said compressed rare gas is analyzed.

According to the invention said rare gas is analyzed by gaseous phase chromatography coupled with mass spectrometry.

Advantageously, said getterizing substrate is a metal alloy in foam, powder, deposition, rod, or ribbon form.

Preferably, said getterizing substrate is a foam or a powder of titanium, zirconium, aluminum or of an alloy of one of these metals.

According to one embodiment of the invention, said getterizing substrate is heated for the step of extraction of said rare gas.

Furthermore, prior to said step of extraction of said rare gas, the vacuum can be produced in a chamber incorporating said getterizing substrate.

Furthermore, the flow rate of the passage of said gaseous fluid in said getterizing substrate can be controlled.

The invention also relates to a system for analyzing at least one gaseous fluid comprising at least one rare gas. The system comprises:

a flow rate restrictor for controlling the flow rate of said gaseous fluid, means for extracting and accumulating said rare gas comprising an accumulation chamber incorporating a getterizing substrate, said getterizing substrate being suitable for trapping all the components of said gaseous fluid apart from said rare gas, means for creating a vacuum in said accumulation chamber, means for compressing said extracted rare gas, the compression means being suitable for compressing and injecting said rare gas for said analysis, and means for analyzing said compressed rare gas.

Advantageously, said gaseous fluid is a sample of gas taken from a geological reservoir.

Advantageously, said means for analyzing said rare gas comprise a chromatograph coupled with a mass spectrometer.

According to an embodiment of the invention, said getterizing substrate is a metal alloy in foam, powder, deposition, rod or ribbon form.

Preferably, said getterizing substrate is a foam or a powder of titanium, zirconium, aluminum or of an alloy of one these metals.

Furthermore, said analysis system can also comprise means for heating said chamber incorporating said getterizing substrate.

According to the invention, said analysis system also comprises vacuum-generating means for said chamber suitable for creating a vacuum in said chamber incorporating said getterizing substrate, said vacuum-generating means comprising at least one pump.

Advantageously, said vacuum-generating means also comprise a second getterizing substrate suitable for trapping the reactive gaseous molecules present in said chamber in a powerful vacuum.

According to a variant embodiment of the invention, said means for compressing said rare gas comprise a superconcentration syringe pump comprising a piston whose displacement can be controlled to adapt the volume and the pressure of said rare gas for said analysis.

Furthermore, said analysis system can comprise a transfer syringe pump suitable for picking up said gaseous fluid and for transferring it to said means for extracting said rare gas, said transfer syringe pump comprising a piston whose displacement can be controlled to adapt the injection flow rate of said fluid into said means for extracting said rare gas.

Moreover, said analysis system can comprise a flow rate restrictor upstream of the means for extracting said rare gas.

BRIEF DESCRIPTION OF THE FIGURES

Other features and advantages of the method according to the invention will become apparent on reading the following description of non-limiting exemplary embodiments, with reference to the attached drawing described below.

FIG. 1 illustrates an embodiment of the analysis system according to the invention.

DETAILED DESCRIPTION OF THE INVENTION

The invention relates to a method for analyzing a gaseous fluid, the gaseous fluid comprising at least one rare gas. The method according to the invention makes it possible to determine, characterize and quantify the rare gases present in the gaseous fluid. Preferably, the gaseous fluid corresponds to a gaseous mixture taken from a geological reservoir containing hydrocarbons. Advantageously, this gaseous fluid is a sample of the gaseous mixture, and the sample can be contained in a vessel of substantially cylindrical form, the ends of which are equipped with at least one valve for releasing and/or sealing a gas in the vessel.

The method for analyzing a gaseous fluid according to the invention comprises the following steps:
1. Extraction of the rare gases
2. Compression of the rare gases
3. Analysis of the rare gases
1. Extraction of the Rare Gases This step makes it possible to separate the rare gases from the other constituents of the gaseous fluid (that is to say the gaseous species that are reactive, by contrast with the rare gases which are inert). For this, the gaseous fluid to be analyzed is injected into means for trapping the other constituents of the gaseous fluid, which make it possible to extract only the rare gases, by trapping the other constituents of the gaseous fluid. In the case of a gaseous fluid from the gas or oil domain, the other constituents are essentially hydrocarbons, $CO_2$ and nitrogen.

According to the invention, the extraction of the rare gases is performed by means of a getterizing substrate. A getter is a substance used to extract, by combination or adsorption of the quantities, generally low, of other substances from a fluid. For example, a metal such as magnesium can be used to extract the final traces of air when producing a powerful vacuum. Different getters are also used to extract the impurities from semiconductors. The term substrate is used in as much as it is a substance which reacts with a reagent (rare gas) to form a product (getter charged with the trapped gases).

The getterizing substrate according to the invention is of the non-evaporable getter type for the purification of gases under pressure, which, through the reactivity of a metal alloy, makes it possible to trap, irreversibly and with constant volume, the trace reactive gaseous molecules present in a pressurized inert gas flow. After passage through the getterizing substrate, it is possible that a few traces of gases other than the rare gases might remain, but these traces are in small quantities and do not hinder the analysis.

Advantageously, the getterizing substrate according to the invention is a metal alloy in foam, powder, deposition, rod or ribbon form. This list is not exhaustive. Preferably, the getterizing substrate is a foam or a powder based on titanium, zirconium, aluminum or based on an alloy of these different metals. In practice, this type of substrate has a high trapping capacity.

The trapping effectiveness of the getterizing principle can be quantified as diazote-normalized mol/cm$^3$. This trapping rate defines the quantity of gas that can be trapped per unit of volume of free gas in a chamber incorporating the getterizing substrate. The volume concept does not therefore relate to the volume occupied by the getterizing substrate but its "connected porosity". This trapping effectiveness is therefore a measurement of the ratio number of mol of trapped gas (Np)/free gas volume (Nl), in the total volume of the getter (NFoG). In order to comprehend this trapping rate, it is essential to consider the form (powder, foam, deposition, rods, ribbons, etc.) and the geometry (spherical, diameter, etc.) of the metal alloy which constitutes the substrate of the getter, as well as the raw trapping potential of this alloy in terms of mol of gas trapped per gram of getter alloy.

The literature contains few trapping potential values for molecules other than dihydrogen. For example, the literature reports, for a Zr—V—Fe alloy, a trapping potential measured in a continuous flow of pressurized ethylene of 160 μmol of carbon per gram of alloy.

Tests performed by the applicant in a laboratory show that a titanium foam substrate can have a trapping potential greater than that given in the literature, of the order of 1000 μmol/g.

The value of 1000 μmol of carbon can be converted into cm$^3$ of gas at standard pressure, which gives 20 cm$^3$. Thus, a gram of getter produced in the form of titanium foam is able to trap up to 20 cm$^3$ of monoatomic reactive gas at atmospheric pressure. By starting from a powder with single radius spherical grain geometry, it is possible to calculate a model porosity for a volume of reagent filled with this alloy powder. This porosity, depending on the way the particles are assembled, will lie within the range 0.50-0.25. It is therefore possible to estimate a high trapping rate value of the order of $1.41 \cdot 10^{-2}$ mol·cm$^{-3}$, or, in volume ratio terms, equal to 346. It is therefore possible to hope to enrich with the rare gas an initial gas by a factor of approximately 350. This enrichment factor does not depend on the volume of the trap, and depends only on the chemical and geometrical properties of the getterizing substrate. This value corresponds to the number of moles of atoms trapped, so it is therefore necessary to weight it with the molecular complexity of the purified gas to determine an effective enrichment factor. For air, therefore the majority molecules are diatomic ($N_2$, $O_2$), the factor must be divided by two, for $CO_2$ by three, and so on.

The invention makes it possible to concentrate the rare gases present in small quantities in a gas source by virtue of the accumulation of the rare gases in a chamber consisting of a non-evaporable getter. According to one embodiment of the invention, the chamber incorporating the getterizing substrate can be initially set to a vacuum. According to the invention, the flow rate of the gaseous fluid is controlled for its passage in the getterizing substrate, and for this the gaseous fluid first passes through a flow rate restrictor. The reactive species that make up the majority of the molarity of the gas to be processed will react with the getter element after their passage from a flow rate restrictor. The instantaneous purification of the reactive species of the gas make it possible to maintain a pressure gradient through the flow rate restrictor, and the accumulation of the rare gases in the accumulation chamber up to the saturation of the getter, or up to the point where a pressure balance is achieved on either side of the flow rate restrictor. Thus, the gas accumulated in the chamber incorporating the getterizing substrate has a partial pressure of rare gases greater than that of the initial gas, according to the following law:

$P_i^{GR} \cdot V_i^{GR} = P_f^{GR} \cdot V_f^{GR}$ with $P_i^{GR}$ being the initial pressure of the rare gases, $V_i^{GR}$ being the initial volume of the rare gases, $P_f^{GR}$ being the final pressure (that is to say, in the chamber incorporating the getterizing substrate) of the rare gases, and $V_i^{GR}$ being the final volume (that is to say, in the chamber incorporating the getterizing substrate) of the rare gases.

Starting from the principle that all of the volume $V_i$ (initial volume of the gaseous fluid, for example volume of the gas sample) is transferred into the volume $V_f$ (gaseous volume in the chamber incorporating the getterizing substrate) and by adopting the principle of conservation of matter, a relationship of the following type can be written:

$$P_f^{GR} = P_i^{GR} \cdot \frac{V_i^{GR}}{V_f^{GR}}.$$

The rare gas enrichment factor $$\frac{P_f^{GR}}{P_i^{GR}},$$

is therefore proportional to the ratio of the volumes $$\frac{V_i^{GR}}{V_f^{GR}},$$

which can be chosen by the user, involving the taking into account of getter mechanical and performance constraints. Thus, the total partial rare gas pressure of a gas sample can be increased very significantly, by means of the getterizing substrate.

This step therefore makes it possible to extract the rare gases from the gaseous fluid by increasing the partial pressure of the rare gases.

Once the getter has been dimensioned, the time-related aspects which will govern the general principle of the getter can be addressed. One factor to be taken into account is clearly kinetics of trapping by getterizing. In practice, this principle is based on a reactivity of the surface alloy with the gaseous phase. This surface reaction reaches saturation when the outer layer of the alloy has entirely reacted through reactions of the following type:

2M+N2→2MN in which M corresponds to a mol of alloy, and N a mol of nitrogen. When the surface layer of the alloy is saturated, the reaction can be continued by virtue of the diffusion of the oxidized alloy in the metal matrix, and therefore the reappearance on the surface of the alloy of native metal (therefore reactive metal). The diffusion process is slower than the kinetics of the surface reaction. It is therefore this diffusion which can constitute a limiting factor on the overall trapping kinetics (therefore adjusted to the weight of alloy). In this kinetics issue, it will be well understood that the aspects of form and of specific surface area of the alloy particles play an important role. A maximized specific surface area of the getter ($m^2/g$) makes it possible to minimize the diffusion-limiting factor. On the other hand, a strong specific surface area very widely increases the porosity of the getter, which is detrimental to the preconcentration factor as defined previously. Moreover, the temperature of the alloy plays an important role with regard to the rates of diffusion in the alloy. It is therefore possible to optimize the choice of the form of the getterizing substrate (the alloy) and its operating temperature in order to optimize the extraction step according to a trio of performance criteria: 1) enrichment rate, 2) implementation time, 3) bulk, while complying with a quantitative specification (initial sample quantity available, sample quantity necessary for the analysis, non-contamination, etc.).

Therefore, in order to make this optimization possible, the method according to the invention can comprise a step of heating of the chamber comprising the getterizing substrate, during the trapping step.

A second kinetic aspect relates to the "pumping" speed of the getter. In practice, the preconcentration principle relies on a pressure differential between the getter and the intake of the gaseous fluid. According to a variant embodiment, the circulation flow rate of the gaseous fluid can be limited for the step of extraction of the rare gases. This limiting can be implemented by a flow rate restrictor, which ensures a pressure differential between the intake of the gaseous fluid and the getter. The dimensioning of the flow rate restrictor makes it possible to create a flow rate in the getter with an order of magnitude similar to the trapping rate of the getter in order to optimize the preconcentration and the trapping speed.

2. Compression of the Rare Gases

The gas extracted from the gaseous fluid is then compressed, such that the pressure and the volume of the rare gases are adapted to the pressure and the volume of the analysis, that is to say to the measuring appliances, which is implemented to determine, quantify and characterize the rare gases present in the gaseous fluid.

According to one embodiment of the invention, the aim is to achieve a target enrichment factor objective of between 100 and 1000, between the partial pressure of the rare gases in the gaseous fluid and the partial pressure of the rare gases after the compression step. To achieve this objective, the trapping capacity of the getterizing substrate has to be well characterized, and a compression of the rare gases, notably through a superconcentration device, has to be adapted to these results. This superconcentration device can consist of a syringe pump for example, via a principle of increasing the pressure of the purified and preconcentrated gas at the getter outlet. The dimensioning of the superconcentration device should incorporate the concept of gas sample quantity ultimately necessary to perform the analysis.

For example, for the application of elemental and isotopic measurement of the rare gases, it is possible to envisage gaseous phase chromatography measurements coupled with mass spectrometry (GC-MS) and/or static mass spectrometry (static MS (quadripolar for example)). Gaseous phase chromatography analysis coupled with mass spectrometry with an isotropic ratio (GC-IRMS) for the isotopy of the carbon for example consumes at most, for each injection, of the order of 10 μL at atmospheric pressure of a 100% $CO_2$ gas. Considering the dilution of scarce rare gases (Ne, Kr, Xe) the majority rare gases (He, Ar) by a factor that can range up to $10^6$ in extreme cases, we have to increase the sample quantity to be injected while considering suitable MS detection methods (detectors of different ranges for the different rare gases and isotopes). For chromatographic reasons, the injection of more than 500 μL seems problematic. It is therefore possible to start from a unitary injection of a volume of 100 μL. For statistical reasons, three injections are desirable for each sample, plus a gas aliquote for the isotopic analysis of the He (optional depending on the final analytical solutions). A quantity of 400 μL therefore seems to be a minimum. Consequently, the compression step has to make it possible to obtain a quantity of at least 400 μl of rare gases for this application.

Moreover, a superconcentration factor can be defined that is equivalent to the rate of pressure increase produced by a syringe pump system. According to the example, this factor is constrained by a final volume of the superconcentrated gas of at least 500 μl. By starting from an initial getter dimension corresponding to a free gas volume $V_f^{GR}$, the concentration rate can be at most:

$$\frac{V_f^{GR}}{500}$$

μl, i.e. for example, for $V_f^{GR}=1000$ μl, the superconcentration factor does not exceed 2. Consequently, for this application, the compression step makes it possible to compress the rare gases, so as to obtain a volume of at least 500 μl with a compression factor of 2.

3. Analysis of the Rare Gases

In order to characterize the gaseous fluid, rare gases included in this fluid are studied. For this study, it is possible to implement an analysis of the extracted and compressed rare gases. According to one embodiment of the invention, this analysis can be implemented by a gaseous phase chromatography coupled with a mass spectrometry (GC-MS) and/or static mass spectrometry (quadripolar or magnetic for example) and/or a gaseous phase chromatography coupled with an isotopic ratios mass spectrometry (GC-IRMS).

The method according to the invention is applicable in the field of the exploitation of geological reservoirs comprising natural gases ($CO_2$, $N_2$, hydrocarbons, helium) or industrially stored gases ($CH_4$, $CO_2$, $H_2$); in fact, based on the results of an analysis of a gas sample taken from a geological reservoir, the gases present in this reservoir can be characterized, and, from this characterization, a possible exploitation of the reservoir can be defined.

The invention also relates to a system for analyzing a gaseous fluid comprising at least one rare gas, the analysis system comprising:
  means for extracting said rare gas comprising a chamber incorporating a getterizing substrate, said getterizing substrate being suitable for trapping all the components of said gaseous fluid apart from said rare gas,
  means for compressing said extracted rare gas, suitable for compressing and injecting said rare gas for said analysis, and
  means for analyzing said compressed rare gas.

As defined previously, the getterizing substrate is of the non-evaporable getter type for the purification of pressurized gas, which, through the reactivity of a metal alloy, makes it possible to trap, irreversibly and at constant volume, the reactive gaseous molecules present in a pressurized inert gas flow. Advantageously, the getterizing substrate is a metal alloy in foam, powder, deposition, rod or ribbon form. This list is not exhaustive. Preferably, the getterizing substrate is a foam or a powder based on titanium, zirconium, aluminum or based on an alloy of these different metals. In fact, this type of substrate exhibits a high trapping capacity.

The gas extracted from the gaseous fluid is then compressed by the compression means, such that the pressure and the volume of the rare gases are adapted to the analysis means, that is to say to the measuring appliances, which are implemented to determine, quantify and characterize the rare gases present in the gaseous fluid. The compression means can comprise a superconcentration syringe pump comprising a piston, whose displacement can be adjusted and controlled to adapt to the volume and the pressure of the rare gas for the analysis. In practice, the position of the piston of the superconcentration syringe pump makes it possible to control the volume and the pressure of the rare gases.

The analysis means can be an aqueous phase chromatograph coupled with a mass spectrometer (GC-MS) and/or a static mass spectrometer (static MS (quadripolar for example)) and/or a gaseous phase chromatograph coupled with an isotopic ratios mass spectrometer (GC-IRMS).

According to one embodiment of the invention, the gaseous fluid is a gas sample. Such a sample can be a vessel of substantially cylindrical form, whose ends are equipped with at least one valve for releasing and/or sealing a gas in the vessel.

Furthermore, the analysis system according to the invention can comprise a transfer syringe pump suitable for picking up the gaseous fluid and for transferring it to the means for extracting said rare gas, the transfer syringe pump comprising a piston whose displacement can be controlled to adapt the injection flow rate of said fluid in said means for extracting said rare gas.

The analysis system according to the invention can also comprise a flow rate restrictor between the intake of the gaseous fluid and the rare gas extraction means. The flow rate restrictor makes it possible to ensure a pressure differential between the gaseous fluid intake and the getter. The dimensioning of the flow rate restrictor makes it possible to create a flow rate toward the getter with an order of magnitude similar to the trapping rate of the getter in order to optimize the preconcentration and the trapping speed.

Furthermore, the system according to the invention can comprise heating means, for example an oven, that make it possible to heat the rare gas extraction means. In practice, the temperature of the getter plays an important role in the rates of diffusion of the particles trapped in the getter alloy. It is therefore possible to optimize the choice of the form of the getterizing substrate (the alloy) and its operating temperature in order to optimize the extraction of the rare gases according to a trio of performance criteria: 1) enrichment rate, 2) implementation time, 3) bulk, while complying with the quantitative specification (initial sample quantity available, sample quantity necessary for the analysis, non-contamination, etc.).

Moreover, the analysis system according to the invention can comprise vacuum-generating means for the chamber suitable for creating a vacuum in said chamber incorporating said getterizing substrate. These vacuum-generating means advantageously comprise a pump. Furthermore, the vacuum-generating means can also comprise a second getterizing substrate suitable for trapping the reactive gaseous molecules present in a chamber in a powerful vacuum. This second getterizing substrate is arranged in the chamber. The vacuum makes it possible to optimize the effectiveness of the getter.

FIG. 1 represents an embodiment of the analysis system according to the invention. According to this embodiment, the analysis system comprises:
- a gas sample (1) (as gaseous fluid),
- a transfer syringe pump (2),
- a flow rate restrictor (3),
- a switching valve (4),
- a chamber incorporating a switching substrate (5),
- an oven (6) as heating means,
- a turbo-pump (7) for creating the vacuum in the chamber (5),
- a superconcentration syringe pump (8),
- analysis means (9) such as a chromatograph coupled with a mass spectrometer,
- a primary pump (10).

In this FIGURE, the symbol P designates a pressure gauge and the circles including crosses represent valves.

For the embodiment of FIG. 1, the analysis can be performed as follows:

Once the sample (1) is connected, the vacuum is created in the first part of the circuit (2, 3) via the primary pump (10) up to a vacuum of the order of $10^{-2}$ mbar. During this step, the switching valve (4) connects the flow rate restrictor (3) with the primary pump (10) and the getter (5) with the superconcentration system (8). For its part, the getter (5) is pumped by the turbo-pump (7), and heated to 800° C. by means of the oven (6), until a secondary vacuum of the order of $10^{-7}$ mbar is achieved.

When these system preparation conditions have been met, the first part of the circuit (2, 3) is isolated from the primary pump (10). The valve of the sample tube (1) is opened on this first part of the circuit (2, 3), and the gas pressure on the pressure gauge is recorded. The volume of the syringe pump (2) is then adjusted according to the necessary sample quantity, at atmospheric pressure.

Then, the isolation valve for isolating the getter (5) from the pumping (7) is closed. The switching valve (4) is switched over, which enables the sample gas contained in the first part of the circuit (2, 3) to circulate at controlled flow rate with the getter (5). The sample gas is thus slowly purified and accumulated in the getter (5). The sample gas will be preconcentrated in the getter (5) until a quantity of gas that is deemed necessary is introduced into the getter (5) (that can be adjusted according to the knowledge of the composition of the raw gas), measured by the displacement of the piston of the transfer syringe pump (2). Once the preconcentration has been performed, the heating of the getter is switched off, and the latter is cooled to room temperature.

Once at room temperature, the switching valve (4) is switched over, which connects the getter (5) with the superconcentration system (8), previously set to a vacuum. The gas is transferred to the superconcentration syringe pump (8) through the action of the piston. Once transferred, the second part of the circuit (8, 9) is isolated, and the gas present in the syringe pump is compressed by the action of the piston, until the volume necessary for the analysis series is obtained.

Finally, the super concentrated gas in the syringe pump (8) is injected toward the analysis instrument (9), and maintained at constant pressure during the different injections through the action of the piston of the syringe pump (8).

The invention claimed is:

1. Method for analyzing a gaseous fluid comprising at least one rare gas, characterized in that the following steps are carried out:
   a) the vacuum is created in an accumulation chamber comprising a getterizing substrate, said getterizing substrate being suitable for trapping the components of said gaseous fluid except for said rare gas;
   b) the flow rate of said fluid entering into said accumulation chamber is controlled by means of a flow rate restrictor;
   c) said rare gas is extracted and accumulated from said gaseous fluid and separated from other components of said gaseous fluid by the passage of said gaseous fluid into said getterizing substrate of said accumulation chamber;
   d) said extracted rare gas, separated from the other components of the gaseous fluid, is compressed such that the pressure and the volume of said compressed rare gas are adapted to the pressure and the volume of said analysis; and
   e) said compressed rare gas, separated from the other components of the gaseous fluid, is analyzed.

2. Method according to claim 1, in which said rare gas is analyzed by gaseous phase chromatography coupled with mass spectrometry.

3. Method according to claim 1, in which said getterizing substrate is a metal alloy in foam, powder, deposition, rod or ribbon form.

4. Method according to claim 3, in which said getterizing substrate is a foam or powder of titanium, zirconium, aluminum or an alloy of one of these metals.

5. Method according to claim 1, in which said getterizing substrate is heated for the step of extraction of said rare gas.

6. Method according to claim 1, in which, prior to said step of extraction of said rare gas, the vacuum is produced in a chamber incorporating said getterizing substrate.

7. Method according to claim 1, in which the flow rate of the passage of said gaseous fluid in said getterizing substrate is controlled.

8. System for analyzing at least one gaseous fluid comprising at least one rare gas, characterized in that it comprises:
   a flow rate restrictor for controlling the flow rate of said gaseous fluid,
   means for extracting and accumulating said rare gas comprising an accumulation chamber incorporating a getterizing substrate, said getterizing substrate being suitable for trapping all the components of said gaseous fluid apart from said rare gas,
   vacuum-generating means for said accumulation chamber, means for compressing said extracted rare gas, separated from the other components of the gaseous fluid, the compression means being suitable for compressing and injecting said rare gas, separated from the other components of the gaseous fluid, for said analysis, and means for analyzing said compressed rare gas, separated from the other components of the gaseous fluid.

9. System according to claim 8, in which said gaseous fluid is a sample of gas taken from a geological reservoir.

10. System according to claim 8, in which said means for analyzing said rare gas comprise a chromatograph coupled with a mass spectrometer.

11. System according to claim 8, in which said getterizing substrate is a metal alloy in foam, powder, deposition, rod or ribbon form.

12. System according to claim 11, in which said getterizing substrate is a foam or a powder of titanium, zirconium, aluminum or an alloy of one of these metals.

13. System according to claim 8, in which said analysis system also comprises means for heating said chamber incorporating said getterizing substrate.

14. System according to claim 8, in which said analysis system also comprises vacuum-generating means for said chamber suitable for creating a vacuum in said chamber incorporating said getterizing substrate, said vacuum-generating means comprising at least one pump.

15. System according to claim 14, in which said vacuum-generating means also comprise a second getterizing substrate suitable for trapping the reactive gaseous molecules present in said chamber in a powerful vacuum.

16. System according to claim 8, in which said means for compressing said rare gas comprise a superconcentration syringe pump comprising a piston whose displacement can be controlled to adapt the volume and the pressure of said rare gas for said analysis.

17. System according to claim 8, in which said analysis system comprises a transfer syringe pump suitable for picking up said gaseous fluid and for transferring it to said means for extracting said rare gas, said transfer syringe pump comprising a piston whose displacement can be controlled to adapt the injection flow rate of said fluid in said means for extracting said rare gas.

18. System according to claim 8, in which said analysis system comprises a flow rate restrictor upstream of the means for extracting said rare gas.

19. A method for analysis of a gaseous fluid comprising at least one rare gas, the at least one rare gas being a sample of gas taken from a geological reservoir, comprising:
a) creating a vacuum in an accumulation chamber comprising a getterizing substrate, the getterizing substrate being configured to trapping components of the gaseous fluid except for rare gas;
b) controlling a flow rate of the gaseous fluid comprising the at least one rare gas entering into the accumulation chamber by a flow rate restrictor;
c) extracting and accumulating the at least one rare gas from the gaseous fluid comprising the at least one rare gas by the passage of the gaseous fluid comprising the at least one rare gas into the getterizing substrate of the accumulation chamber;
d) compressing the at least one rare gas that has been extracted and accumulated in the accumulation chamber from the gaseous fluid and that has been separated from the other components of the gaseous fluid such that a pressure and volume of the at least one rare gas are adapted to a pressure and volume of the analysis; and
e) analyzing the at least one rare gas, separated from the other components of the gaseous fluid, at the pressure and volume to which the at least one rare gas has been compressed.

20. The method according to claim 19, wherein analyzing the at least one rare gas is conducted by gaseous phase chromatography coupled with mass spectrometry.

21. A system for analysis of at least one gaseous fluid comprising at least one rare gas, comprising:
an accumulation chamber incorporating a getterizing substrate, the getterizing substrate being configured to trap all components of the at least one gaseous fluid comprising the at least one rare gas apart from rare gas to separate the at least one rare gas from other components of the at least one gaseous fluid,
a flow rate restrictor for controlling a flow rate of the at least one gaseous fluid comprising the at least one rare gas into the accumulation chamber,
a first pump for creating a vacuum in the accumulation chamber,
a second pump for compressing the at least one rare gas that has been extracted and accumulated in the accumulation chamber from the gaseous fluid and that has been separated from the other components of the at least one gaseous fluid such that a pressure and volume of the at least one rare gas are adapted to a pressure and volume of the analysis, and
at least one analyzer for analyzing the at least one rare gas that has been separated from the other components of the at least one gaseous fluid at the pressure and volume to which the at least one rare gas has been compressed by the pump for compressing the at least one rare.

22. The system according to claim 21, wherein the at least one analyzer comprises a gaseous phase chromatograph coupled with a mass spectrometer.

23. The system according to claim 22, further comprising a gas sample source, taken from a geological reservoir, operably connected to the accumulation chamber for supplying the at least one gaseous fluid comprising the at least one rare gas.

24. The system according to claim 21, further comprising a gas sample source, taken from a geological reservoir, operably connected to the accumulation chamber for supplying the at least one gaseous fluid comprising the at least one rare gas.

* * * * *